US012743946B2

(12) United States Patent
A N et al.

(10) Patent No.: US 12,743,946 B2
(45) Date of Patent: Sep. 22, 2026

(54) SYSTEMS AND METHODS FOR A SMART REMOTE-CONTROL DEVICE FOR USERS IN NEED OF ASSISTANCE

(71) Applicant: DISH Network Technologies India Private Limited, Bangalore (IN)

(72) Inventors: Srinidhi A N, Bangalore (IN); PraveenKumar G, Bangalore (IN); Sreevastav Anupuru, Bangalore (IN); Ramegowda Thimmegowda, Bangalore (IN)

(73) Assignee: DISH NETWORK TECHNOLOGIES INDIA PRIVATE LIMITED, Bangalore (IN)

( * ) Notice: Subject to any disclaimer, the term of this patent is extended or adjusted under 35 U.S.C. 154(b) by 58 days.

(21) Appl. No.: 18/669,134

(22) Filed: May 20, 2024

(65) Prior Publication Data

US 2025/0356752 A1 Nov. 20, 2025

(51) Int. Cl.

| | |
|---|---|
| ***G08B 25/01*** | (2006.01) |
| ***A61B 5/00*** | (2006.01) |
| ***G16H 50/30*** | (2018.01) |
| ***G16H 80/00*** | (2018.01) |
| ***H04N 21/422*** | (2011.01) |
| ***H04N 21/4415*** | (2011.01) |

(52) U.S. Cl.
CPC .......... *G08B 25/016* (2013.01); *A61B 5/0002* (2013.01); *G16H 50/30* (2018.01); *G16H 80/00* (2018.01); *H04N 21/42222* (2013.01); *H04N 21/4415* (2013.01)

(58) Field of Classification Search
CPC .... G08B 25/016; A61B 5/0002; G16H 50/30; G16H 80/00; H04N 21/42222; H04N 21/4415
See application file for complete search history.

(56) References Cited

U.S. PATENT DOCUMENTS

| | | | | |
|---|---|---|---|---|
| 6,225,938 | B1 * | 5/2001 | Hayes | H04N 5/775 235/462.46 |
| 6,419,630 | B1 * | 7/2002 | Taylor, Jr. | A61B 5/7475 128/920 |
| 10,147,304 | B1 * | 12/2018 | Lazarski | G08B 21/0269 |
| 2009/0146779 | A1 * | 6/2009 | Kumar | G08C 17/02 340/5.31 |
| 2016/0252901 | A1 * | 9/2016 | Harary | E06B 9/24 700/275 |
| 2020/0043594 | A1 * | 2/2020 | Miller | G16H 20/60 |
| 2022/0054088 | A1 * | 2/2022 | Cheung Hyen | A61B 5/6898 |
| 2024/0221546 | A1 * | 7/2024 | Batta | G09F 13/22 |

* cited by examiner

*Primary Examiner* — Rufus C Point
(74) *Attorney, Agent, or Firm* — Seed Intellectual Property Law Group LLP

(57) ABSTRACT

Systems and methods for using a remote-control device to determine whether a user is in need of assistance are provided herein. A remote-control device may include at least one health data sensor. The remote-control device may be configured to receive health data regarding a user operating the remote-control device via the health data sensor and determine whether the user is in need of assistance based on the health data. The remote-control device may transmit an indication that the user is in need of assistance to a computing device based on a determination that the user is in need of assistance.

20 Claims, 6 Drawing Sheets

SYSTEMS AND METHODS FOR A SMART REMOTE-CONTROL DEVICE FOR USERS IN NEED OF ASSISTANCE

BACKGROUND

Certain populations of people, such as seniors, people with disabilities, hospital patients, or other populations, receive consistent monitoring of vital signs to determine whether a person is in need of assistance, such as medical assistance or other assistance. Additionally, such populations of people may be more likely to spend more time using remote-control devices, such as to control a television or other device. It is with respect to this and other considerations that the embodiments described herein have been made.

BRIEF SUMMARY

The embodiments disclosed herein improve the technology of remote-control devices by providing a technical solution that determines whether a user of the remote-control device is in need of assistance based on health signs, vital signs, etc., (collectively "vital signs") of the user. The embodiments disclosed herein may utilize a remote-control device that includes one or more health data sensors that generate health data indicating a remote-control device user's vital signs. Furthermore, the embodiments disclosed herein may cause an indication that a user is in need of assistance to be transmitted to a computing device, such as a computing device associated with a caretaker of the user of the remote-control device.

In some embodiments, a remote-control device may be configured to receive an indication of an identity of a user of the remote-control device from a set-top box associated with the remote-control device. The remote-control device may receive an indication of a threshold measure of vital signs based on the identify of the user. The remote-control device may use the threshold measure of vital signs and health data associated with the user to determine whether the user is in need of assistance. In some embodiments, the remote-control device may include a biometric identification sensor. In such embodiments, the user may be identified based on biometric data generated by the biometric identification sensor.

In some embodiments, the remote-control device includes one or more programmable buttons. Activation of one or more programmable buttons may cause the remote-control device to control a device. The remote-control device may receive an indication of a device that is to be controlled by the one or more programmable buttons. The remote-control device may configure itself to control the device in response to activation of one or more programmable buttons.

In some embodiments, the remote-control device includes one or more emergency buttons. In such embodiments, the remote-control device may detect that an emergency button has been pressed. In response to detecting that the emergency button has been pressed, the remote-control device may transmit an indication that the user of the remote-control device requires emergency assistance.

In some embodiments, the remote-control device includes one or more biometric identification sensors. The remote-control device may determine an identity of a user based on data received from the one or more biometric identification sensors. The remote-control device may cause a set-top box to access a profile associated with the identified user by transmitting a signal to the set-top box that the identified user is using the remote-control device.

In some embodiments, the remote-control device includes one or more movement sensors. In such embodiments, data generated by the one or more movement sensors may be used to determine whether the remote-control device is being handled by a user. In response to determining that the remote-control device is being handled by the user, at least one health data sensor associated with the remote-control device may be activated.

In some embodiments, a set-top box may be configured to receive data from a remote-control device that includes health data regarding a user operating the remote-control device. The set-top box may use the health data to determine whether the user is in need of assistance. Based on a determination that the user is in need of assistance, the set-top box transmits an indication that the user is in need of assistance to a computing device.

In some embodiments, the set-top box may identify a user based on a user profile currently logged into the set-top box. In some embodiments, the set-top box may identify a user based on biometric identity data generated by one or more biometric identification sensors. In some embodiments, the set-top box configures the remote-control device to control a device. In some embodiments, the set-top box access a user profile based on identification data of a user of the remote. In some embodiments, the set-top box transmits an indication that the user is in need of emergency assistance to a computing device. In some embodiments, the set-top box activates one or more sensors of the remote-control device based on movement data generated by one or more movement sensors.

DETAILED DESCRIPTION

Figure 1:
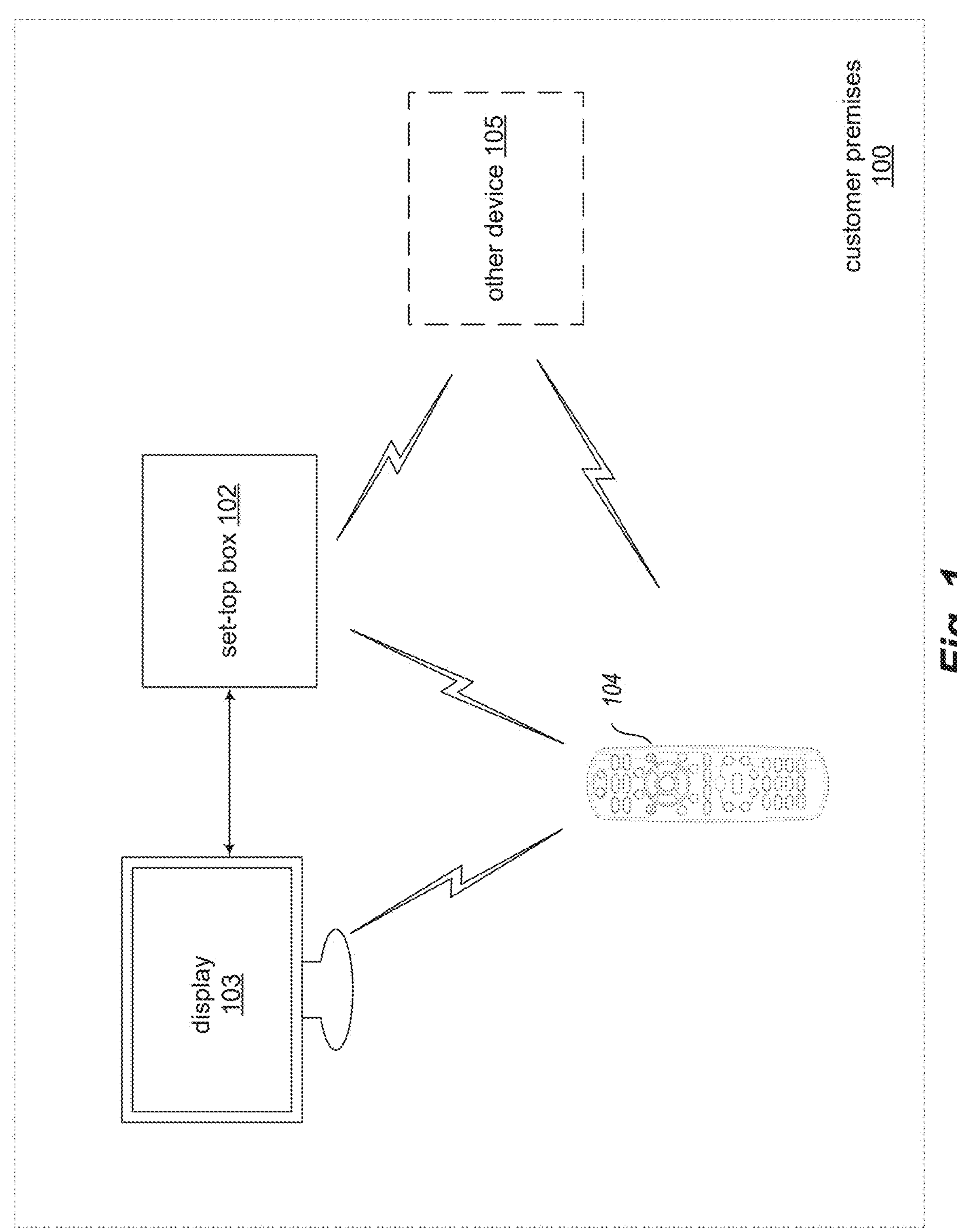
FIG. 1 is a display diagram of a sample customer premises within which the remote-control device and set-top box operate, according to various embodiments described herein.

Certain populations of people receive consistent monitoring of their vital signs, such as seniors, people with disabilities, hospital patients, and other populations of people that may receive consistent monitoring of vital signs (collectively "at-risk populations of people"), to detect whether such a person is in need of assistance. Conventional methods of monitoring such vital signs of a person include attaching one or more medical devices to the person, receiving video or audio data of the person, and other intrusive methods of monitoring vital signs of a person. Furthermore, many people included in at-risk populations are wary, uncomfortable, or otherwise averse to such intrusive methods of monitoring such vital signs.

The embodiments disclosed herein improve the technology of remote-control devices by providing a technical solution that determines whether a user of the remote-control device is in need of assistance based on health signs, vital signs, etc., (collectively "vital signs") of the user. The embodiments disclosed herein may utilize a remote-control device that includes one or more health data sensors that generate health data indicating a remote-control device user's vital signs. Furthermore, the embodiments disclosed herein may cause an indication that a user is in need of assistance to be transmitted to a computing device, such as a computing device associated with a caretaker of the user of the remote-control device.

Unless the context requires otherwise, throughout the specification and claims which follow, the word "comprise" and variations thereof, such as, "comprises" and "comprising" are to be construed in an open, inclusive sense, for example "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Furthermore, the particular features, structures, or characteristics may be combined in any suitable manner in one or more embodiments, and references to "some embodiments," "other embodiments," "example embodiments," "one embodiment," "an embodiment," etc., do not preclude the combination of the particular features, structures, or characteristics of any of the embodiments with any of the other embodiments described herein.

As used in this specification and the appended claims, the singular forms "a," "an," and "the" include plural referents unless the content clearly dictates otherwise. The term "or" is generally employed to include "and/or" unless the content clearly dictates otherwise. The term "and/or" is generally employed to include an inclusive or.

The headings and Abstract of the Disclosure provided herein are for convenience only and do not interpret the scope or meaning of the embodiments.

FIG. 1 is a display diagram of a sample customer premises 100 within which the remote-control device and set-top box operate, according to various embodiments described herein. It is to be appreciated that FIG. 1 illustrates just one example of a customer premises 101 environment and that the various embodiments discussed herein are not limited to the use of such environment. The customer premises 101 can include a variety of communication systems and can use a variety of communication devices, presentation devices and media including, but not limited to, media provided by satellite, cable, and Internet streaming services.

Audio, video, and/or data service providers, such as, but not limited to, television service providers, provide their customers a multitude of audio/video and/or data programming (hereafter, collectively and/or exclusively "programming"). Such programming is often provided by use of a set-top box 102 communicatively coupled to a display 103 configured to receive the programming.

The set-top box 102 may interconnect to one or more communications media or sources, such as a cable head-end, satellite antenna, telephone company switch, Ethernet portal, off-air antenna, or the like, that provide the programming. The set-top box 102 commonly receives a plurality of programming by way of the communications media or other sources. Based upon selection by the user, the set-top box 102 processes and communicates the selected programming to the one or more displays 103.

The set-top box 102 may include devices such as a "television converter," "receiver," "set-top box," "television receiving device," "television receiver," "television recording device," "digital video recorder (DVR)," "satellite set-top box," "satellite receiver," "cable set-top box," "cable receiver," "media player," "Internet streaming device," "television tuner," "media receiver," and/or "media playback device." Accordingly, the set-top box 102 may be any suitable converter device or electronic equipment that is operable to receive and/or play programming. Further, the set-top box 102 may itself include user interface devices, such as buttons, switches and displays. In many applications, a remote-control device 104 is operable to control the display 103 and communicate with the set-top box 102.

Examples of a display 103 include, but are not limited to, a television ("TV"), a personal computer ("PC"), a monitor, a touch screen, a game system, or the like. A display 103 may employ one or more speakers (not shown) and/or other output devices to communicate video and/or audio content to a user (not shown). In many implementations, one or more displays 103 reside in or near a customer's premises 101 and are communicatively coupled, directly or indirectly, to the set-top box 102. Further, the set-top box 102 and the display 103 may be integrated into a single device. Such a single device may have the functionality of the set-top box 102 described herein and the display 103, or may even have additional functionality.

The set-top box 102 may receive a signal from a communications media or source. The set-top box 102 may be a conversion device that converts, also referred to as formatting, the received signal into a signal suitable for communication to a display 103.

The set-top box 102 may receive programming partially from, or entirely from, another source other than that described above. Other embodiments of the set-top box 102 may receive locally broadcast RF signals, or may be coupled to a communications system via any suitable medium. Non-limiting examples of medium communicatively coupling the set-top box 102 to a communications system include cable, fiber optic, or Internet media.

Customer premises 101 may include other devices which are communicatively coupled to the set-top box 102 and/or a communication system via a suitable media, such as the other device 105. Non-limiting examples of the other device 105 include, but are not limited to: an "internet of things" or "smart" device, such as a smart light, a smart appliance, a robot, or other internet of things or smart devices; a "hub" device, such as a Google Home device, Google Nest, iHome, or other hub devices; a computing system; a tablet computer; a video gaming system; an endpoint device; or another device that can communicate with a receiving device, remote-control device, or network. For example, some customer premises 101 include an optional network, communication system or networked system (not shown), to which set-top box 102 and display 103 can be coupled, collectively referred to as endpoint devices. Non-limiting examples of such a network or communication system include, but are not limited to, an Ethernet system, twisted pair Ethernet system, an intranet, a local area network ("LAN") system, short range wireless network (e.g., Bluetooth®), a personal area network (e.g., a Zigbee network based on the IEEE 802.15.4 specification), a Consumer Electronics Control (CEC) communication system or the like. One or more endpoint devices, such as PCs, data storage devices, TVs, game systems, sound system receivers, Internet connection devices, digital subscriber loop ("DSL") devices, wireless LAN, WiFi, Worldwide Interoperability for Microwave Access ("WiMax") devices, or the like, may be communicatively coupled to the network or to each other so that the plurality of endpoint devices are communicatively coupled together. Thus, such a network allows the other device 105 device and the set-top box 102, to communicate with each other. Alternatively, or in addition, some devices in the customer premises 101 may be directly connected to the network, such as a telephone which may employ a hardwire connection or an RF signal for coupling to the network, which may also connect to other networks or communications systems outside customer premises 101.

A hand-held remote-control device 104 may provide an interface between the set-top box 102 and a user. In some embodiments, the remote-control device 104 may be configured to provide an interface between the other device 105 and the user. Remote-control device 104 typically communicates with the set-top box 102 using a suitable wireless medium, such as infrared ("IR"), radio frequency ("RF"), or the like and may be any wireless handheld device, including a mobile device such as a cellular telephone or a tablet device. Other input or control devices (not shown) may also be communicatively coupled to the set-top box 102. Non-limiting examples include game device controllers, keyboards, touch pads, touch screens, pointing devices and the like. The remote-control device 104 may also control other devices such as the display 103 and/or other endpoint devices (not shown). The remote-control device 104 may be a "universal" remote or otherwise programmable or configurable by a manufacturer, user, and/or other device to control such other devices.

In some embodiments, the remote-control device 104 may be a multibrand remote that comes to the user preprogrammed with the codes to operate a number of standard home electronic devices. Such a remote may be able to control multiple devices and, in some embodiments, control their main functions, such as channel turning, volume control and other functions. The remote-control device 104 may also be a "learning" remote. In particular, while the remote-control device 104 may be preprogrammed to operate a number of popular electronic models, it may also have the ability to learn the functions of the original manufacturer's remote of each device. For example, this may be accomplished by placing the remote-control device 104 head-to-head with the device's original manufacturer's remote and infrared signals will be transmitted to the learning remote that allow it to duplicate the other remote's commands. Such learning can also be accomplished via RF or wired communication between remote-control devices and/or other devices.

In some embodiments, the remote-control device 104 can receive signals from the set-top box 102. In many such embodiments, the remote-control device 104 can also execute instructions contained in the signals received from the set-top box 102. In some embodiments, the remote-control device 104 transmit data to another device 105, the set-top box 102, the display 103, another device, such as a computing device associated with a facility within which the user is located, or some combination thereof. In some embodiments, remote-control device 104 can control any of the devices to which it can transmit data.

The above description of the customer premises 101, and the various devices therein, is intended as a broad, non-limiting overview of an example environment in which various embodiments of the systems and methods described herein may operate. The customer premises 101 and the various devices therein, may contain other devices, systems and/or media not specifically described herein.

Example embodiments described herein provide applications, tools, data structures and other support to implement the systems and methods described herein. The example embodiments described herein additionally provide applications, tools, data structures and other support to implement the systems and methods described herein to monitor vital signs of a user of the remote-control device and determine whether the user is in need of assistance. Other embodiments of the described techniques may be used for other purposes, including for controlling the operation of remote-control devices generally. In the following description, numerous specific details are set forth in order to provide a thorough understanding of the described techniques. The embodiments described also can be practiced without some of the specific details described herein, or with other specific details, such as changes with respect to the ordering of processes or devices, different processes or devices, and the like. Thus, the scope of the techniques and/or functions described are not limited by the particular order, selection, or decomposition of steps described with reference to any particular module, component, or routine.

Figure 2:
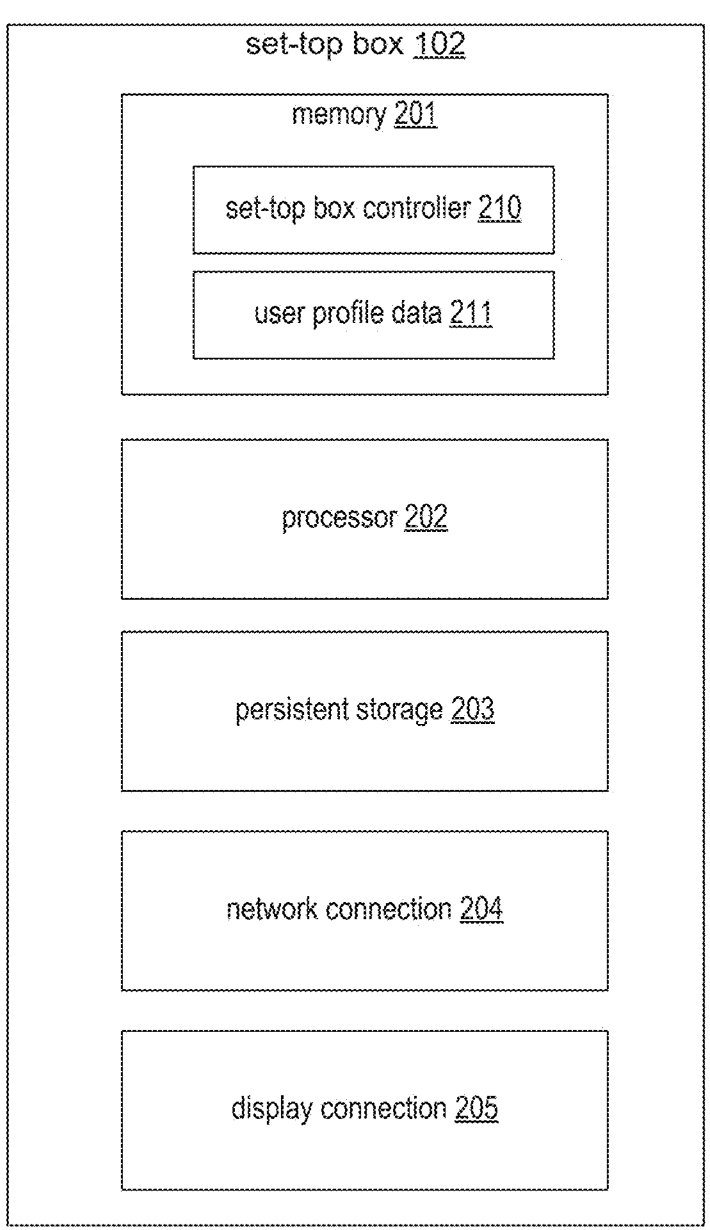
FIG. 2 is a display diagram of a sample set-top box, according to various embodiments described herein.

FIG. 2 is a display diagram of a sample set-top box 102, according to various embodiments described herein. In various embodiments, the set-top box 102 includes one or more of the following: a processor 201 for executing computer programs; a computer memory 202 for storing programs and data while they are being used, including the facility and associated data, an operating system including a kernel, and device drivers; a persistent storage device 203, such as a hard drive or flash drive for persistently storing programs and data; a network connection 204 for connecting the computer system to satellite, cable, and Internet streaming services, remote control devices, such as remote control device 104, and/or other computer systems to send and/or receive data, such as via the Internet or another network and its networking hardware, such as switches, routers, repeaters, electrical cables and optical fibers, light emitters and receivers, radio transmitters and receivers, and the like; and a display connection 205 for causing visual information or data to be displayed, such as on display 103, to a user. While a set-top box 102 configured as described above is typically used to support the operation of the systems and methods described herein, those skilled in the art will appreciate that the facility may be implemented using devices of various types and configurations, and having various components.

The memory 201 may have computer-executable instructions stored thereon, that, when executed by the processor 201, cause the set-top box 102 and/or remote-control device 104 to perform the operations and functions described herein. The memory 201 may also include a set-top box controller 210 (the "controller 210") and user profile data 211. In particular, the set-top box controller 210 may perform any one or more of the aspects of the systems and methods described herein, such as determining whether a user is in need of assistance, identifying threshold vital signs for a user, identifying an identity of a user, changing or accessing a profile of a user that is logged into the set-top box 102, or other aspects of the systems and methods described herein.

The user profile data 211 includes data associated with one or more user profiles that may be logged in to the set-top box 102. Such data may include, but is not limited to: data regarding one or more threshold vital signs associated with the user; biometric identification data used to identify the user; one or more devices, such as the other device 105, that the user may control via a remote-control device; one or more computing devices associated with a caretaker of the user; one or more emergency services that the user may contact via the remote-control device; other data associated with a user that may be stored by the set-top box 102; or some combination thereof.

In an example embodiment, the controller 210 or computer-executable instructions stored on memory 201 of the set-top box 102 are implemented using standard programming techniques. For example, the controller 210 or computer-executable instructions stored on memory 201 of the set-top box 102 may be implemented as a "native" executable running on CPU 202, along with one or more static or dynamic libraries. In other embodiments, the controller 210 or computer-executable instructions stored on memory 201 of the set-top box 102 may be implemented as instructions processed by a virtual machine that executes as some other program.

The embodiments described above may also use synchronous or asynchronous client-server computing techniques. However, the various components may be implemented using more monolithic programming techniques as well, for example, as an executable running on a single processor computer system, or alternatively decomposed using a variety of structuring techniques known in the art, including but not limited to, multiprogramming, multithreading, client-server, or peer-to-peer, running on one or more computer systems each having one or more processors. Some embodiments may execute concurrently and asynchronously, and communicate using message passing techniques. Equivalent synchronous embodiments are also supported. Also, other functions could be implemented or performed by each component/module, and in different orders, and by different components/modules, yet still achieve the functions of the network configuration controller 200.

In addition, programming interfaces to the data stored as part of the controller 210 can be available by standard mechanisms such as through C, C++, C #, Java, and web APIs; libraries for accessing files, databases, or other data repositories; through scripting languages such as JavaScript and VBScript; or through Web servers, FTP servers, or other types of servers providing access to stored data. The controller 210 may be implemented by using one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions of the set-top box 102.

Furthermore, in some embodiments, some or all of the components/portions of the controller 210, or functionality provided by the computer-executable instructions stored on memory 201 of the set-top box 102 may be implemented or provided in other manners, such as at least partially in firmware or hardware, including, but not limited to, one or more application-specific integrated circuits (ASICs), standard integrated circuits, controllers (e.g., by executing appropriate instructions, and including microcontrollers or embedded controllers), field-programmable gate arrays (FPGAs), complex programmable logic devices (CPLDs), and the like. Some or all of the system components or data structures may also be stored as contents (e.g., as executable or other machine-readable software instructions or structured data) on a computer-readable medium (e.g., as a hard disk; a memory; a computer network or cellular wireless network; or a portable media article to be read by an appropriate drive or via an appropriate connection, such as a DVD or flash memory device) so as to enable or configure the computer-readable medium or one or more associated computing systems or devices to execute or otherwise use or provide the contents to perform at least some of the described techniques. Such computer program products may also take other forms in other embodiments. Accordingly, embodiments of this disclosure may be practiced with other computer system configurations.

In general, a range of programming languages may be employed for implementing any of the functionality of the client devices, access points, interface mitigation system, interfering devices, etc., present in the example embodiments, including representative implementations of various programming language paradigms and platforms, including but not limited to, object-oriented (e.g., Java, C++, C #, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, PHP, Python, JavaScript, VBScript, and the like) and declarative (e.g., SQL, Prolog, and the like).

Figure 3:
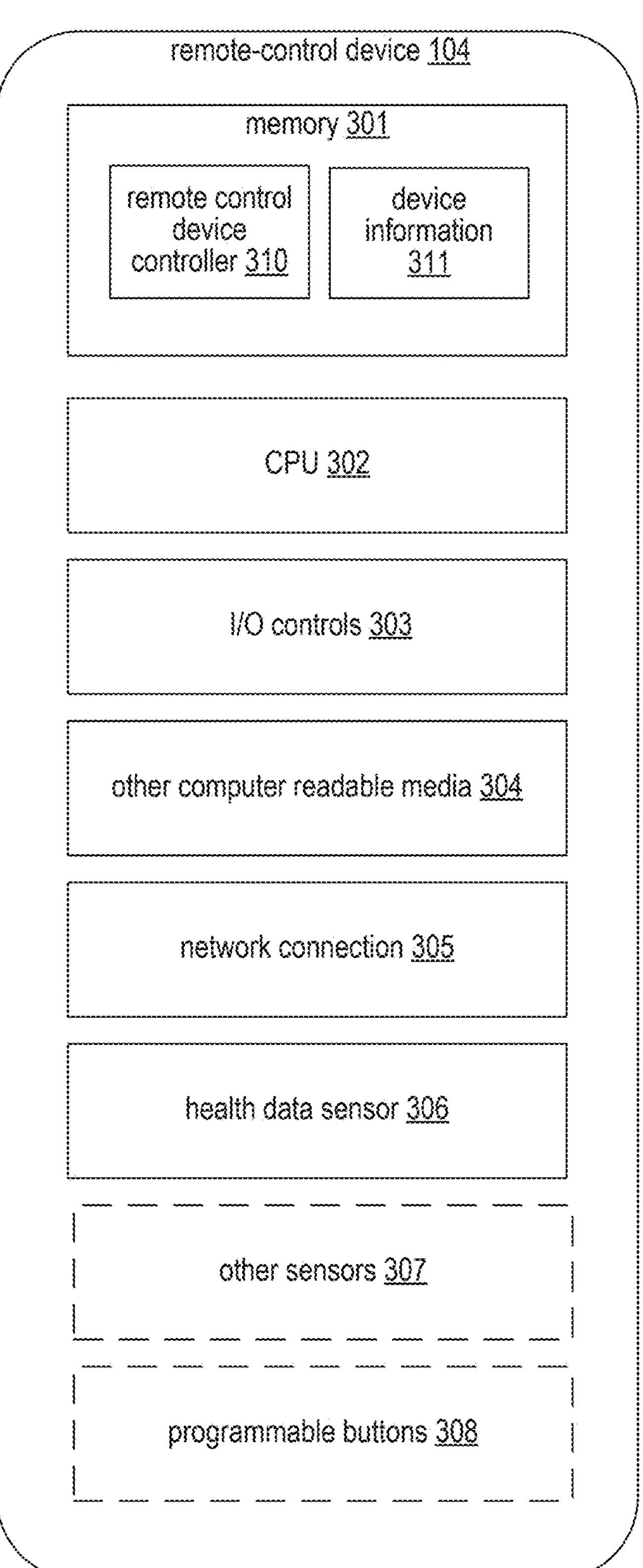
FIG. 3 is a display diagram of a sample remote-control device, according to various embodiments described herein.

FIG. 3 is a display diagram of a sample remote-control device 104, according to various embodiments described herein. In some embodiments, the remote-control device 104 comprises a computer memory ("memory") 301 and one or more Central Processing Units ("CPU") 302. Also included are Input/Output "I/O" controls 303, including, but not limited to: buttons, virtual buttons, switches, keypads, keyboards, touchpads, touchscreens, display screens, liquid crystal displays, speakers, scroll wheel inputs, optical sensors, gesture sensors, accelerometers, motion control sensors, voice command sensors, microphones, track ball's and/or joysticks, etc. The remote-control device 104 may also include other computer-readable media 304 (e.g., flash memory, SIM card) and a network connection 305. For example, the I/O controls 303 may include buttons, although different numbers and configurations of controls exist in various embodiments, including those with touch screen buttons and other input controls. The network connection 305 includes one or more communication interfaces to various media devices, including but not limited to, radio frequency transceivers, infrared transceivers, wireless Ethernet ("Wi-Fi") interfaces, short range wireless (e.g., Bluetooth®) interfaces and the like. The one or more Central Processing Units ("CPU") 302 may be communicatively coupled to the memory 301, the Input/Output controls 303, other computer-readable media 304 and network connection 305, (e.g., via a communications bus) in a manner to control one or more operations of those various components.

The remote-control device 104 may communicate with the set-top box 102, display 103, other device 105, and possibly other computing devices or media devices, such as via the network connection 305. Example media devices include other remote-control devices, media players, streaming media devices, DVRs, DVD players, video recorders, audio systems, displays, personal computers, set-top boxes, mobile devices and the like.

The memory 301 includes a remote-control device controller 310 and device information 311. The remote-control device controller 310 may operate, be configured, or some combination thereof, in a similar manner to the controller 210 described above in connection with FIG. 2. The device information 311 may include information regarding one or more devices that the remote-control device 104 is able to control, such as the set-top box 102, display 103, other device 105, other devices, or some combination thereof. In some embodiments, the memory 301 includes at least some data similar to the data stored in the memory 201 of the set-top box 102, described above in connection with FIG. 2. In some embodiments, at least some of the data stored in the memory 201 of the set-top box 102 is similar to the data stored in the memory 301 of the remote-control device 104.

The remote-control device controller 310 may perform the core functions of the remote-control device 104, as discussed herein and also with respect to FIGS. 4-6 described below. The remote-control device controller 310 may read input that results from activation of I/O controls 303 on the remote-control device 104 by the user and performs the function corresponding to the input, including sending commands to various devices and performing internal operations of the remote-control device 104.

The remote-control device 104 may receive signals at the network connection 305 representing commands to perform operations in the remote-control device 104. These commands can include additional logic regarding the actions taken by remote-control device 104 after activation of certain I/O controls 303, such as preventing the function corresponding to the input from being performed.

In at least some embodiments, remote and/or programmatic access is provided to at least some of the functionality of the remote-control device 104. For example, the remote-control device 104 may provide to other media devices an application program interface ("API") that provides access to various functions of the remote-control device 104, including access to information stored by the remote-control device 104 such as whether functions of the remote are currently disabled.

The remote-control device 104 may further include at least one health data sensor 306. The health data sensor 306 may be one or more of: a sensor that detects a pulse of a user of the remote-control device; a sensor that detects an oxygen level of a user of the remote-control device; a sensor that detects a temperature of a user of the remote-control device; a sensor that detects other health data or vital signs of a user of the remote-control device; or some combination thereof.

In some embodiments, the remote-control device 104 includes other sensors 307. The other sensors 307 may be one or more of: a biometric identification sensor, such as a fingerprint reader, iris scanner, face detection camera, other sensors that may be used to detect biometric identification data associated with a user of the remote-control device, or some combination thereof; a movement sensor, such as a gyroscope, accelerometer, other sensor for detecting movement of a remote-control device, or some combination thereof; other sensors that may be used for detecting data associated with the systems and methods described herein; or some combination thereof.

In some embodiments, where the remote-control device includes a biometric identification sensor, the biometric data received via the biometric identification sensor may be used to cause the remote-control device 104, set-top box 102, other devices or displays, or some combination thereof, to identify, access, switch to, or otherwise use, a profile associated with a user from which the biometric data is received. In such embodiments, the remote-control device 104, set-top box 102, other devices or displays, or some combination thereof may be caused to display a message to a user regarding the use of the profile associated with the user from which the biometric data is received. For example, the set-top box 102 may be caused to display to a user a prompt requesting permission to switch the user profile currently logged in to the set-top box 102 to another user profile associated with the user for which the biometric data is received.

In some embodiments, any of the sensors included in the remote-control device, such as the health data sensor 306 and other sensors 307, may be placed in one or more locations on the remote-control device, such as: a side of the remote-control device; a front of the remote-control device; a back of the remote-control device; on top of, underneath, within, or some combination thereof, a button included in the remote-control device; or some combination thereof.

In some embodiments, the remote-control device 104 includes one or more programmable buttons 308. In such embodiments, the programmable buttons 108 may be configured to: cause the remote-control device to control one or more devices, such as the other device 105; cause a message to be transmitted to an emergency service; cause another action to be taken by the remote-control device 104, set-top box 102, or other device; or some combination thereof. Although the programmable buttons 308 are described as buttons in FIG. 3, embodiments are not so limited, and the programmable buttons 308 may be or include any programmable I/O controls, such as I/O controls similar to one or more of the I/O controls 303.

In some embodiments, activating a programmable button causes the remote-control device to transmit a signal to a device or emergency service. In some embodiments, the remote-control device uses one or more protocols to transmit the signal to a device or emergency service, such as the Matter protocol. In some embodiments, the remote-control device transmits a signal to a set-top box that instructs the set-top box to control the device or contact the emergency service.

In some embodiments, activating a programmable button causes the remote-control device to transmit data to a set-top box indicating that the programmable button was pressed. In such embodiments, the set-top box may transmit a signal to a device or emergency service. In some such embodiments, the set-top box, remote-control device, or some combination thereof, may transmit a signal to a computing device associated with an emergency service, a computing device associated with a caretaker of the user of the remote-control device, or some combination thereof. In some embodiments, a user profile stored in the memory 301 of the remote-control device 104, memory 201 of the set-top box 102, or some combination thereof, includes an indication of one or more functions of the programmable buttons. For example, a particular button may cause a light in one room to turn on or off if a particular user profile is in use, and may cause an appliance to be activated or deactivated if another user profile is in use.

In some embodiments, the set-top box 102, remote-control device 104, or some combination thereof receives an indication that a device is to be controlled by one or more programmable buttons 308. In some embodiments, the set-top box 102, remote-control device 104, or some combination thereof may configure the one or more programmable buttons 308 to control the device. In some embodiments, the set-top box 102, remote-control device 104, or some combination thereof may alter a user profile to indicate that the one or more programmable buttons 308 are to be used to control the device when the user profile is logged in.

The operation of certain aspects will now be described with respect to FIGS. 4-6. In at least one of various embodiments, processes 400, 500, and 600 described in conjunction with FIGS. 4-6, respectively, may be implemented by one or more processors or executed via circuitry on one or more computing devices, such as the set-top box 102 described in connection with FIG. 2, the remote-control device 104 described in connection with FIG. 3, other computing devices, or some combination thereof.

Figure 4:
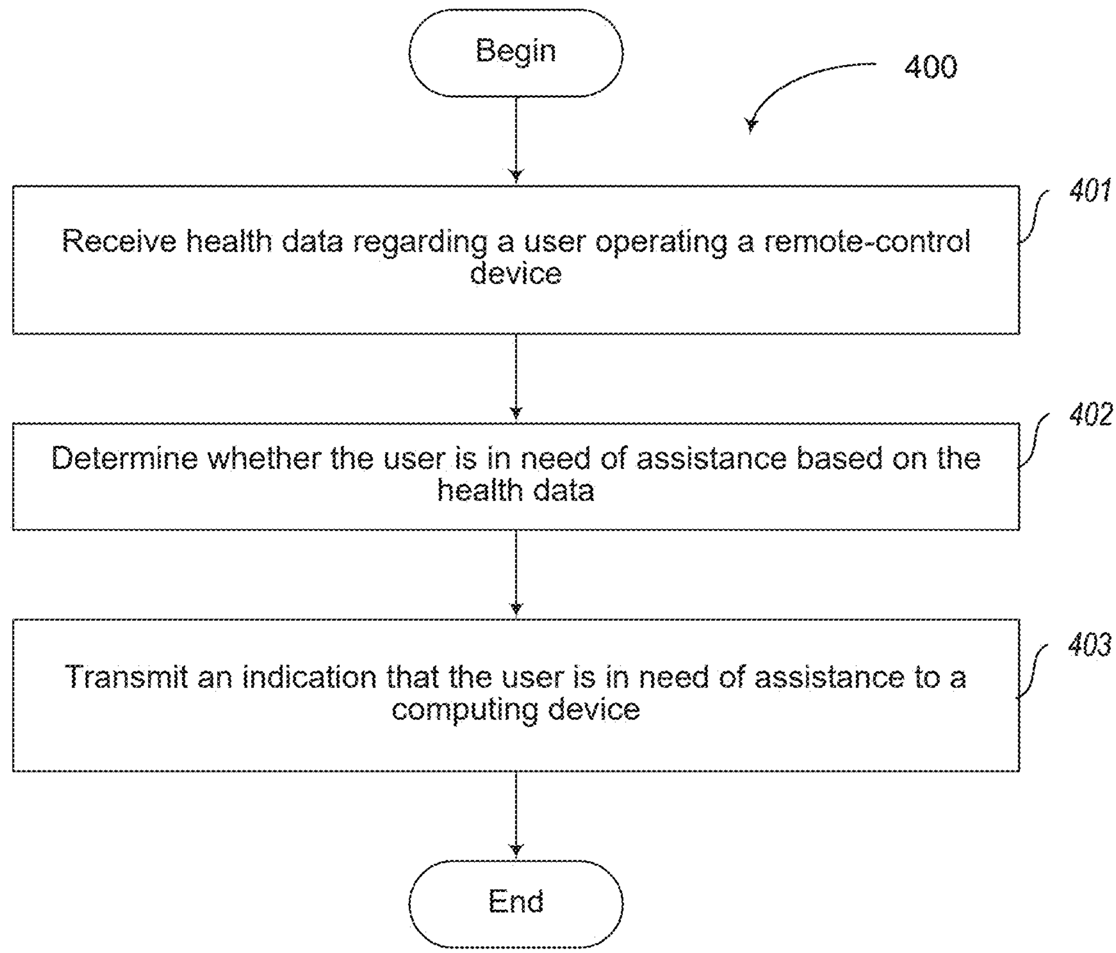
FIG. 4 is a flow diagram of a sample process to determine whether a user of a remote-control device is in need of assistance, according to various embodiments described herein.

FIG. 4 is a flow diagram of a sample process 400 to determine whether a user of a remote-control device is in need of assistance, according to various embodiments described herein. Although the process 400 is described as being performed by the remote-control device 104, embodiments are not so limited, and aspects of the process 400 may be performed by a set-top box, such as the set-top box 102 described above in connection with FIG. 2, a remote-control device, such as the remote-control device 104 described above in connection with FIG. 3, other computing device, or some combination thereof.

The process 400 begins, after a start block, at act 401, where the remote-control device receives health data regarding a user operating a remote-control device. The remote-control device may receive the health data via a health data sensor included in the remote-control device, such as the health data sensor 306 described above in connection with FIG. 3.

The process 400 proceeds to act 402, where the remote-control device determines whether the user is in need of assistance based on the health data. In some embodiments, the user is determined to be in need of assistance if the health data indicates that at least one of the user's vital signs has exceeded a threshold level. In some embodiments, the user is determined to be in need of assistance if the health data indicates that at least one of the user's vital signs has exceeded a threshold level for a threshold amount of time.

The process 400 proceeds to act 403, where the remote-control device transmits an indication that the user is in need of assistance to a computing device. In some embodiments, the computing device is a computing device associated with a caretaker of the user of the remote-control device. In some embodiments, the computing device is a computing device associated with one or more emergency services. In some embodiments, the indication that the user is in need of assistance includes an indication of a location of the user. In such embodiments, the location of the user may be determined based on one or more of: a location sensor, such as a GPS receiver, included in the remote-control device; a last known device to receive a signal from the remote-control device; a network access point to which the remote-control device is connected; other methods of determining a location of a user; or some combination thereof.

After act 403, the process 400 ends. In some embodiments, instead of performing act 402, the remote-control device transmits an indication of the health data to a computing device associated with a caretaker of the user. In such embodiments, the computing device associated with the caretaker may be used to determine whether the user is in need of assistance, such as by displaying the health data to a caretaker, comparing the health data to one or more threshold measures of vital signs, or some combination thereof.

Figure 5:
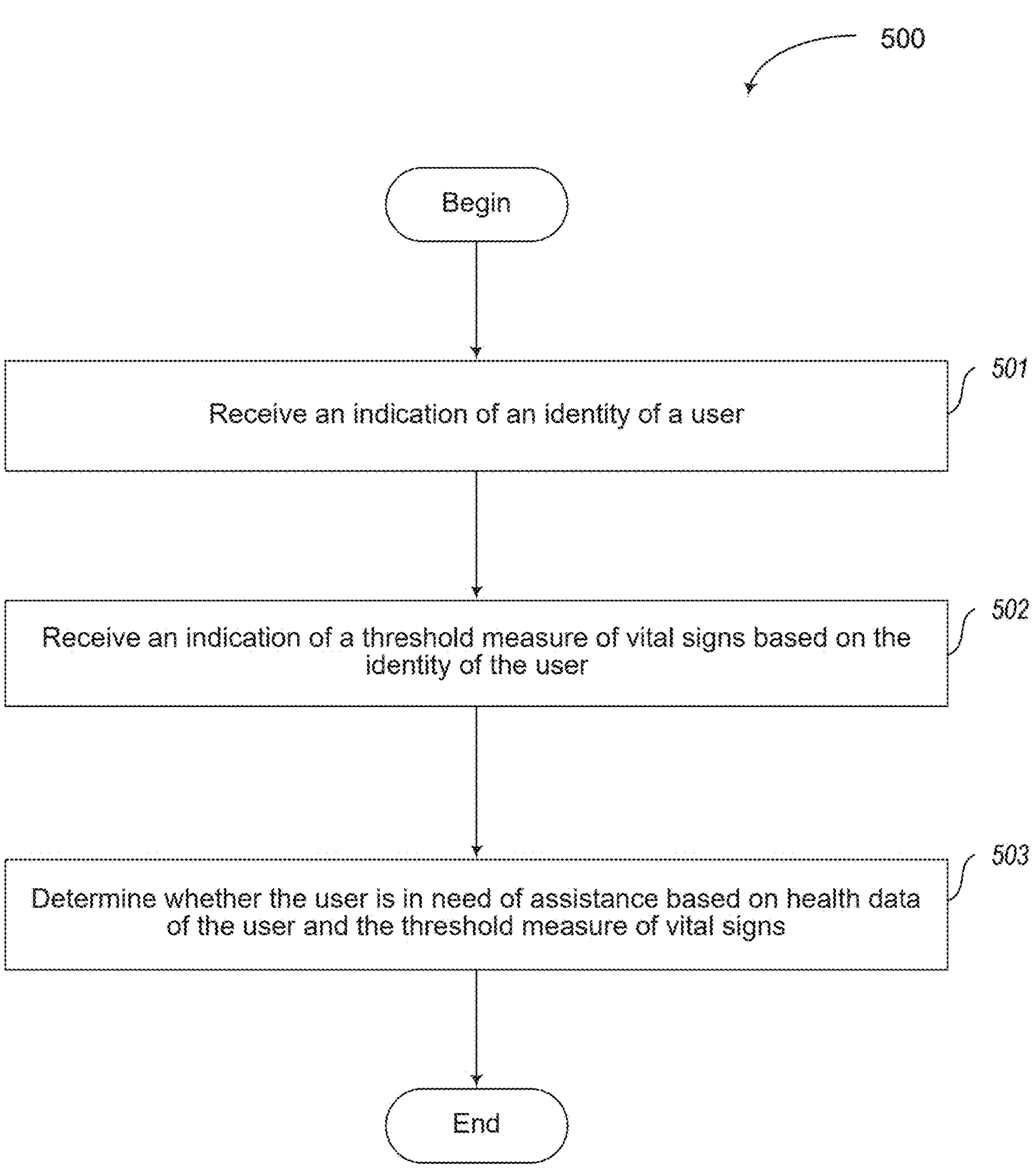
FIG. 5 is a flow diagram of a sample process to obtain a threshold measure of vital signs for a user, according to various embodiments described herein.

FIG. 5 is a flow diagram of a sample process 500 to obtain a threshold measure of vital signs for a user, according to various embodiments described herein. Although the process 500 is described as being performed by the remote-control device 104, embodiments are not so limited, and aspects of the process 500 may be performed by a set-top box, such as the set-top box 102 described above in connection with FIG. 2, a remote-control device, such as the remote-control device 104 described above in connection with FIG. 3, other computing device, or some combination thereof.

The process 500 begins, after a start block, at act 501, where the remote-control device receives an indication of an identity of a user. In some embodiments, the indication of the identity of the user is received from a set-top box, such as the set-top box 102. In such embodiments, the identity of the user may be determined based on a user profile currently logged into the set-top box. In some embodiments, the indication of the identity of the user is received from a biometric identification sensor, such as, for example, a biometric identification sensor included in the remote-control device. In such embodiments, the biometric identification sensor may generate biometric data used to identify the user. The biometric data may be used to identify a user, such as by comparing the generated biometric data to stored biometric data associated with the user. The stored biometric data may be stored in the remote-control device, set-top box, another computing device, or some combination thereof.

In some embodiments, the remote-control device causes the set-top box to change the profile of the user logged in to the set-top box based on received indication of the identity of the user. For example, the remote-control device may transmit instructions to the set-top box to log in a user profile associated with a user for whom biometric data was generated by a biometric identification sensor.

In some embodiments, the remote-control device receives information regarding the user, such as information stored in a user profile associated with the user, based on the received identity data of the user. In such embodiments, the remote-control device may receive the information regarding the user even if the user profile associated with the user is not currently logged into the set-top box. For example, if a user profile associated with a first user is logged into the set-top box, and the remote-control device detects, via a biometric identification sensor, that a second user is handling the remote-control device, the information retrieved is information regarding the second user and not the first user. In such an example, the user profile associated with the first user may remain to be logged in to the set-top box, but information regarding the second user, such as a threshold measure of vital signs, devices configured by the second user to be controlled by the remote-control device, emergency contacts of the second user, other information regarding the second user, or some combination thereof, may be accessed by the remote-control device.

The process 500 proceeds to act 502, where the remote-control device receives an indication of a threshold measure of vital signs based on the identity of the user. In some embodiments, the threshold measure of vital signs includes a threshold period of time during which the vital signs of a user are able to exceed the threshold measure of vital signs. In some embodiments, the threshold measure of vital signs is not dependent on a user and are at a default level for all users. In some embodiments, the threshold measure of vital signs is stored by the remote-control device, set-top box, or some combination thereof. In such embodiments, one or more threshold measures of vital signs may be associated with one or more users.

In some embodiments, the threshold measure of vital signs is stored by a computing device associated with a caretaker of the user. In such embodiments, the set-top box, remote-control device, or some combination thereof, may transmit an indication of the identity of the user to the computing device and may receive the threshold measure of vital signs from the computing device. In some embodiments, the threshold measure of vital signs is generated based on one or more health attributes of a user associated with the user profile, such as an age, a weight, a height, a resting heart rate, a resting breathing rate, a health condition that the user has, other health attributes, or some combination thereof.

The process 500 proceeds to act 503, where the remote-control device determines whether the user is in need of assistance based on health data associated with the user and the threshold measure of vital signs. Act 503 may be performed in a similar manner to act 402, described above in connection with FIG. 4.

After act 503, the process 500 ends.

Figure 6:
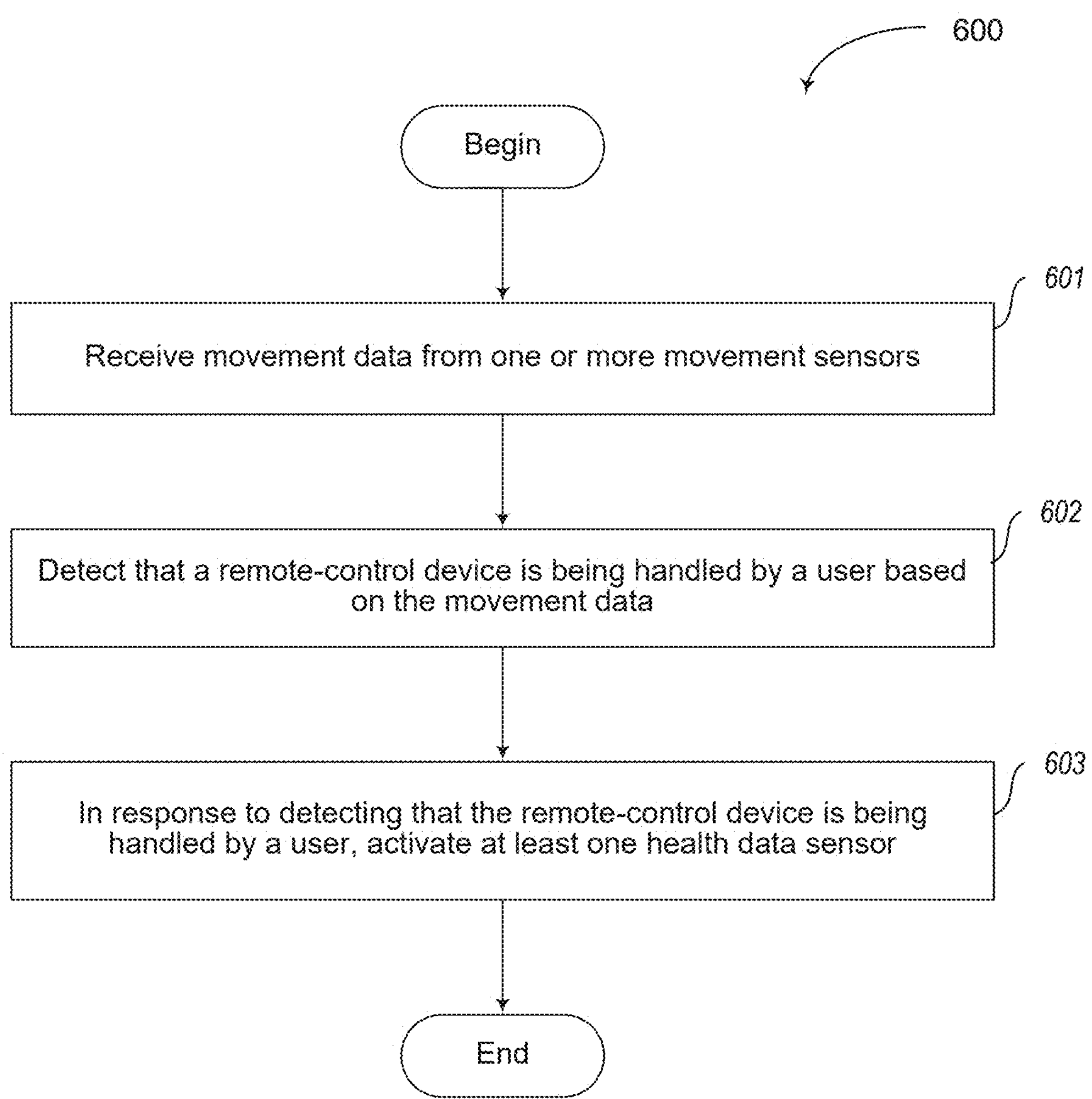
FIG. 6 is a flow diagram of a sample process to activate at least one health data sensor, according to various embodiments described herein.

FIG. 6 is a flow diagram of a sample process 600 to activate at least one health data sensor, according to various embodiments described herein. Although the process 600 is described as being performed by the remote-control device 104, embodiments are not so limited, and aspects of the process 600 may be performed by a set-top box, such as the set-top box 102 described above in connection with FIG. 2, a remote-control device, such as the remote-control device 104 described above in connection with FIG. 3, other computing device, or some combination thereof.

The process 600 begins, after a start block, at act 601, where the remote-control device receives movement data from one or more movement sensors. In some embodiments, at least a portion of the one or more movement sensors are included in the remote-control device.

The process 600 proceeds to act 602, where the remote-control device detects that the remote-control device is being handled by a user based on the movement data. For example, the movement data may indicate that the remote-control device fell, such as by indicating that the remote-control device accelerated quickly while rotating, before coming to a sudden stop. In such an example, the remote-control device may determine that it is not being handled by the user. In another example, the movement data may indicate that a user raised the remote and pointed it at a display, such as by indicating that the remote-control device moved at a steady rate of speed until it stopped moving and stayed level throughout the movement. In such an example, the remote-control device may determine that it was being handled by the user.

The process 600 proceeds to act 603, where the remote-control device activates at least one health data sensor in response to detecting that the remote-control device is being handled by a user. In some embodiments, the remote-control device activates one or more other sensors in response to detecting that the remote-control device is being handled by a user, such as a biometric identification sensor.

After act 603, the process 600 ends.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A remote-control device, comprising:
- at least one input control;
- at least one health data sensor;
- at least one transmitter for transmitting signals to a receiving device;
- two or more programmable input controls;
- at least one processor; and
- at least one memory coupled to the at least one processor, the memory having computer-executable instructions stored thereon that, when executed by the at least one processor, cause the remote-control device to:
  - receive an indication of a device that is to be controlled by a first programmable input control of the two or more programmable input controls;
  - configure the remote-control device to control the device by using the Matter smart home protocol when user input is received via the first programmable input control;
  - configure the remote-control device to cause one or more signals indicating that the user is in need of assistance to be transmitted directly to a computing device via a wireless network by using the Matter smart home protocol when user input is received via a second programmable input control of the two or more programmable input controls;
  - receive input from a user via the at least one input control;
  - transmit, via the transmitter, one or more signals to control the receiving device based on the received input;
  - receive, via the at least one health data sensor, health data regarding a user operating the remote-control device;
  - determine whether the user is in need of assistance based on the health data;
  - based on a determination that the user is in need of assistance:
    - generate one or more signals indicating that the user is in need of assistance; and
    - cause the one or more signals indicating that the user is in need of assistance to be transmitted directly to the computing device via a wireless network by using the Matter smart home protocol; and
  - based on the receipt of input via the second programmable input control:

generate the one or more signals indicating that the user is in need of assistance; and cause the one or more signals indicating that the user is in need of assistance to be transmitted directly to the computing device via the wireless network by using the Matter smart home protocol.

2. The remote-control device of claim 1, wherein the computer-executable instructions further cause the remote-control device to:

receive an indication of an identity of the user from a set-top box associated with the remote-control device;

receive an indication of a threshold measure of vital signs based on the identity of the user; and determine whether the user is in need of assistance based on the health data and the threshold measure of vital signs.

3. The remote-control device of claim 1, wherein the remote-control device further comprises a biometric identification sensor, and wherein the computer-executable instructions further cause the remote-control device to:

determine an identity of the user based on data received from the biometric identification sensor;

receive an indication of a threshold measure of vital signs based on the identity of the user; and determine whether the user is in need of assistance based on the health data and the threshold measure of vital signs.

4. The remote-control device of claim 1, wherein the remote-control device further comprises one or more programmable input controls, and wherein the computer-executable instructions further cause the remote-control device to:

receive an indication of a device that is to be controlled by the one or more programmable input controls; and configure the remote-control device to control the device when user input is received via the one or more programmable input controls.

5. The remote-control device of claim 1, wherein the remote-control device further comprises one or more emergency input controls, and wherein the computer-executable instructions further cause the remote-control device to:

detect that the one or more emergency input controls have been pressed; and in response to detecting that the one or more emergency input controls have been pressed, transmit an indication that the user of the remote-control device requires emergency assistance.

6. The remote-control device of claim 1, wherein the remote-control device further comprises a biometric identification sensor, and wherein the computer-executable instructions further cause the remote-control device to:

determine an identity of the user based on data received from the biometric identification sensor; and cause a set-top box to access a profile associated with the identified user by transmitting a signal to the set-top box that the identified user is using the remote-control device.

7. The remote-control device of claim 1, wherein the remote-control device further comprises one or more movement sensors, and wherein the computer-executable instructions further cause the remote-control device to:

receive movement data from the one or more movement sensors;

detect that the remote-control device is being handled by a user based on the movement data; and in response to detecting that the remote-control device is being handled by the user, activate the at least one health data sensor.

8. A set-top box, comprising:

at least one processor; and at least one memory coupled to the at least one processor, the memory having computer-executable instructions stored thereon that, when executed by the at least one processor, cause the set-top box to:

receive an indication of a device that is to be controlled by a first programmable input control of two or more programmable input controls of a remote-control device;

configure the remote-control device to control the device by using an Internet of things protocol when user input is received via the first programmable input control;

configure the remote-control device to cause one or more signals indicating that the user is in need of assistance to be transmitted directly to a computing device via a wireless network by using the Matter smart home protocol when user input is received via a second programmable input control of the two or more programmable input controls;

receive data from the remote-control device, the received data including health data regarding a user operating the remote-control device;

determine whether the user is in need of assistance based on the health data;

based on a determination that the user is in need of assistance:

cause one or more signals indicating that the user is in need of assistance to be generated; and cause the remote-control device to transmit the one or more signals indicating that the user is in need of assistance to the computing device via a wireless network by using the Internet of things protocol; and based on the receipt of data from the remote-control device indicating that a user has activated the second programmable input:

cause one or more signals indicating that the user is in need of assistance to be generated; and cause the remote-control device to transmit the one or more signals indicating that the user is in need of assistance to a computing device via a wireless network by using the Internet of things protocol.

9. The set-top box of claim 8, wherein the computer-executable instructions further cause the set-top box to:

identify a user based on a user profile that is currently logged in to the set-top box;

receive an indication of a threshold measure of vital signs based on the identity of the user; and determine whether the user is in need of assistance based on the health data and the threshold measure of vital signs.

10. The set-top box of claim 8, wherein the computer-executable instructions further cause the set-top box to:

receive biometric identity data from the remote-control device;

determine an identity of the user based on the biometric identity data;

receive an indication of a threshold measure of vital signs based on the identity of the user; and determine whether the user is in need of assistance based on the health data and the threshold measure of vital signs.

11. The set-top box of claim 8, wherein the computer-executable instructions further cause the set-top box to:
receive an indication of a device that is to be controlled by the remote-control device; and
configure the set-top box to control the device in response to a device control signal received from the remote-control device.

12. The set-top box of claim 8, wherein the computer-executable instructions further cause the set-top box to:
receive an indication of an emergency signal from the remote-control device; and
in response to receiving the indication of the emergency signal, transmit an indication that the user of the remote-control device requires emergency assistance.

13. The set-top box of claim 8, wherein the computer-executable instructions further cause the set-top box to:
receive biometric identity data from the remote-control device;
determine an identity of the user based on the biometric identity data; and
access a profile associated with the identified user.

14. A non-transitory computer-readable media that stores at least one of instructions or data, the instructions or data, when executed by at least one processor, cause the at least one processor to perform a method comprising:
receive an indication of a device that is to be controlled by a first programmable input control of two or more programmable input controls of a remote-control device;
configure the remote-control device to control the device by using a smart home protocol when user input is received via the first programmable input control;
configure the remote-control device to cause one or more signals indicating that the user is in need of assistance to be transmitted directly to a computing device via a wireless network by using the smart home protocol when user input is received via a second programmable input control of the two or more programmable input controls;
receiving, via at least one health data sensor, health data regarding a user operating the remote-control device;
determining whether the user is in need of assistance based on the health data;
based on a determination that the user is in need of assistance:
causing one or more signals indicating that the user is in need of assistance to be generated; and
causing the remote-control device to transmit the one or more signals indicating that the user is in need of assistance to the computing device via a wireless network by using a smart home protocol; and
based on the receipt of input via the second programmable input control:
causing one or more signals indicating that the user is in need of assistance to be generated; and
causing the remote-control device to transmit the one or more signals indicating that the user is in need of assistance to a computing device via a wireless network by using a smart home protocol.

15. The non-transitory computer-readable media of claim 14, wherein the method further comprises:
receiving an indication of an identity of the user;
receiving an indication of a threshold measure of vital signs based on the identity of the user; and
determine whether the user is in need of assistance based on the health data and the threshold measure of vital signs.

16. The non-transitory computer-readable media of claim 14, wherein method further comprises:
determine an identity of the user based on data received from a biometric identification sensor;
receive an indication of a threshold measure of vital signs based on the identity of the user; and
determine whether the user is in need of assistance based on the health data and the threshold measure of vital signs.

17. The non-transitory computer-readable media of claim 14, wherein method further comprises:
receive an indication of a device that is to be controlled by a remote-control device; and
configure the remote-control device to control the device.

18. The non-transitory computer-readable of claim 14, wherein method further comprises:
receive a signal indicating that the user is experiencing an emergency; and
in response to detecting that the user is experiencing an emergency, transmit an indication that the user requires emergency assistance.

19. The non-transitory computer-readable media of claim 14, wherein method further comprises:
determine an identity of the user based on data received from a biometric identification sensor; and
cause a set-top box to access a profile associated with the identified user by transmitting a signal to a set-top box indicating the identified user.

20. The non-transitory computer-readable media of claim 14, wherein method further comprises:
receiving movement data from one or more movement sensors;
detecting that a remote-control device is being handled by a user based on the movement data; and
in response to detecting that the remote-control device is being handled by the user, activate the at least one health data sensor.

* * * * *